US008283342B2

(12) United States Patent
Puig Duran et al.

(10) Patent No.: US 8,283,342 B2
(45) Date of Patent: Oct. 9, 2012

(54) NAPADISYLATE SALT OF 5-(2-{[6-(2,2-DIFLUORO-2-PHENYLETHOXY) HEXYL] AMINO}-1-HYDROXYETHYL)-8-HYDROXYQUINOLIN-2(1H)-ONE AS AGONIST OF THE β2 ADRENERGIC RECEPTOR

(75) Inventors: Carlos Puig Duran, Barcelona (ES); Enrique Moyes Valls, Barcelona (ES)

(73) Assignee: Almirall S.A., Barcelona (ES)

( * ) Notice: Subject to any disclaimer, the term of this patent is extended or adjusted under 35 U.S.C. 154(b) by 195 days.

(21) Appl. No.: 12/526,090

(22) PCT Filed: Feb. 8, 2008

(86) PCT No.: PCT/EP2008/000975
§ 371 (c)(1),
(2), (4) Date: Oct. 8, 2009

(87) PCT Pub. No.: WO2008/095720
PCT Pub. Date: Aug. 14, 2008

(65) Prior Publication Data
US 2011/0195943 A9 Aug. 11, 2011

(30) Foreign Application Priority Data
Feb. 9, 2007 (ES) .................... 200700362

(51) Int. Cl.
A01N 43/42 (2006.01)
A01N 45/00 (2006.01)
A61K 31/44 (2006.01)
A61K 31/56 (2006.01)
A61K 9/14 (2006.01)
C07D 215/00 (2006.01)

(52) U.S. Cl. ......... 514/171; 514/312; 546/157; 424/489
(58) Field of Classification Search ................ 514/171, 514/312; 546/157
See application file for complete search history.

(56) References Cited

U.S. PATENT DOCUMENTS

| | | |
|---|---|---|
| 3,007,923 A | 11/1961 | Muller et al. |
| 3,053,865 A | 9/1962 | Taub et al. |
| 3,104,246 A | 9/1963 | Amiard et al. |
| 3,678,137 A | 7/1972 | Pfeiffer et al. |
| 3,929,768 A | 12/1975 | Brattsand et al. |
| 3,970,677 A | 7/1976 | Nishimura et al. |
| 3,975,391 A | 8/1976 | Nakagawa et al. |
| 3,994,901 A | 11/1976 | Nakagawa et al. |
| 4,022,776 A | 5/1977 | Nakagawa et al. |
| 4,022,784 A | 5/1977 | Nakagawa et al. |
| 4,026,897 A | 5/1977 | Nakagawa et al. |
| 4,068,076 A | 1/1978 | Nakagawa et al. |
| 4,145,542 A | 3/1979 | Nakagawa et al. |
| 4,753,962 A | 6/1988 | Ainsworth et al. |
| 4,992,474 A | 2/1991 | Skidmore et al. |
| 4,997,986 A | 3/1991 | Mitchell et al. |
| 5,099,068 A | 3/1992 | Mitchell et al. |
| 5,109,023 A | 4/1992 | Mitchell et al. |
| 5,201,308 A | 4/1993 | Newhouse |
| 5,263,475 A | 11/1993 | Altermatt et al. |
| 5,283,262 A | 2/1994 | Mitchell et al. |
| 5,435,301 A | 7/1995 | Herold et al. |
| 5,482,934 A | 1/1996 | Calatayud et al. |
| 5,507,281 A | 4/1996 | Kuhnel et al. |
| 5,617,845 A | 4/1997 | Poss et al. |
| 5,685,294 A | 11/1997 | Gupte et al. |
| 6,541,669 B1 | 4/2003 | Moran et al. |
| 7,498,321 B2 | 3/2009 | Biggadike et al. |
| 7,964,615 B2 | 6/2011 | Puig Duran et al. |
| 2002/0055651 A1 | 5/2002 | Moran et al. |
| 2003/0136405 A1 | 7/2003 | Goede et al. |
| 2003/0153597 A1 | 8/2003 | Moran et al. |
| 2004/0059116 A1 | 3/2004 | Moran et al. |
| 2004/0167167 A1 | 8/2004 | Mammen et al. |
| 2005/0043337 A1 | 2/2005 | Rito et al. |
| 2005/0159448 A1 | 7/2005 | McKinnell et al. |
| 2005/0192316 A1 | 9/2005 | Moran et al. |
| 2005/0215590 A1 | 9/2005 | Brown et al. |
| 2005/0272769 A1 | 12/2005 | Linsell |
| 2006/0019991 A1 | 1/2006 | McKinnell et al. |
| 2006/0035931 A1 | 2/2006 | Chao et al. |
| 2006/0081246 A1 | 4/2006 | Goede et al. |
| 2006/0178410 A1 | 8/2006 | Moran et al. |
| 2006/0205949 A1* | 9/2006 | Dalziel et al. ................. 546/209 |

(Continued)

FOREIGN PATENT DOCUMENTS

| | | |
|---|---|---|
| DE | 2 236 272 | 2/1973 |
| DE | 2 310 140 | 9/1974 |
| DE | 2 461 861 | 8/1975 |
| DE | 4 239 402 | 5/1994 |
| EP | 0 069 715 | 1/1983 |
| EP | 0 147 719 | 7/1985 |
| EP | 0 166 294 | 1/1986 |
| EP | 0 286 242 | 10/1988 |
| EP | 0 317 206 | 5/1989 |
| EP | 0 424 790 | 5/1991 |

(Continued)

OTHER PUBLICATIONS

Williams et al (Foye's Principles of Medicinal Chemistry, 5th Edition, pp. 59-63, 2002).*

(Continued)

*Primary Examiner* — Shengjun Wang
*Assistant Examiner* — Uma Ramachandran
(74) *Attorney, Agent, or Firm* — Finnegan, Henderson, Farabow, Garrett & Dunner LLP

(57) ABSTRACT

The present disclosure relates to crystalline monoapadisylate and/or heminapadisylate salt of 5-(2-{[6-(2,2-difluoro-2-phenylethoxy)hexyl]amino}-1-hydroxyethyl)-8-hydroxyquinolin-2(1H)-one, and pharmaceutically acceptable solvates thereof. The present disclosure also relates to pharmaceutical compositions comprising the crystalline monoapadisylate and/or heminapadisylate salt of 5-(2-{[6-(2,2-difluoro-2-phenylethoxy)hexyl]amino}-1-hydroxyethyl)-8-hydroxyquinolin-2(1H)-one, and to methods of treatment comprising these pharmaceutical compositions.

4 Claims, 3 Drawing Sheets

U.S. PATENT DOCUMENTS

| | | | |
|---|---|---|---|
| 2007/0197536 | A1 | 8/2007 | Dal Piaz et al. |
| 2009/0042933 | A1 | 2/2009 | Duran et al. |
| 2009/0082378 | A1 | 3/2009 | Puig Duran et al. |
| 2010/0168161 | A1 | 7/2010 | Tana et al. |
| 2010/0324000 | A1 | 12/2010 | Giulio Matassa et al. |
| 2011/0028442 | A1 | 2/2011 | Puig Duran et al. |
| 2011/0251165 | A1 | 10/2011 | Puig Duran et al. |
| 2011/0251166 | A1 | 10/2011 | Puig Duran et al. |
| 2011/0251234 | A1 | 10/2011 | Carreta Carreta et al. |
| 2012/0004414 | A1 | 1/2012 | Marchueta Hereu et al. |
| 2012/0029014 | A1 | 2/2012 | Ruf et al. |
| 2012/0040941 | A1 | 2/2012 | Ruf et al. |

FOREIGN PATENT DOCUMENTS

| | | |
|---|---|---|
| EP | 0 505 321 | 9/1992 |
| EP | 0 674 533 | 10/1995 |
| EP | 1 078 629 | 2/2001 |
| EP | 1 235 787 | 9/2002 |
| EP | 1 577 291 | 9/2005 |
| ES | 2 232 306 | 5/2005 |
| GB | 0 869 511 | 5/1961 |
| GB | 1 200 886 | 8/1970 |
| GB | 1 247 370 | 9/1971 |
| GB | 1 458 251 | 12/1976 |
| GB | 1 468 156 | 12/1976 |
| GB | 2 041 763 | 9/1980 |
| GB | 2 140 800 | 12/1984 |
| GB | 2 160 863 | 1/1986 |
| GB | 2 165 159 | 4/1986 |
| GB | 2 242 134 | 9/1991 |
| JP | 51 149 282 | 12/1976 |
| JP | 59 093 051 | 5/1984 |
| WO | WO 91/02558 | 3/1991 |
| WO | WO 91/14468 | 10/1991 |
| WO | WO 92/00771 | 1/1992 |
| WO | WO 92/03175 | 3/1992 |
| WO | WO 92/04068 | 3/1992 |
| WO | WO 92/04928 | 4/1992 |
| WO | WO 92/09322 | 6/1992 |
| WO | WO 96/32150 | 10/1996 |
| WO | WO 97/00703 | 1/1997 |
| WO | WO 97/12687 | 4/1997 |
| WO | WO 98/09632 | 3/1998 |
| WO | WO 99/30703 | 6/1999 |
| WO | WO 99/64035 | 12/1999 |
| WO | WO 01/36375 | 5/2001 |
| WO | WO 01/42193 | 6/2001 |
| WO | WO 02/066422 | 8/2002 |
| WO | WO 02/070490 | 9/2002 |
| WO | WO 02/092606 | 11/2002 |
| WO | WO 03/000325 | 1/2003 |
| WO | WO 03/042160 | 5/2003 |
| WO | WO 03/061742 | 7/2003 |
| WO | WO 03/072539 | 9/2003 |
| WO | WO 03/091204 | 11/2003 |
| WO | WO 03/097613 | 11/2003 |
| WO | WO 03/099764 | 12/2003 |
| WO | WO 2004/011416 | 2/2004 |
| WO | WO 2004/016578 | 2/2004 |
| WO | WO 2004/058729 | 7/2004 |
| WO | WO 2004/089892 | 10/2004 |
| WO | WO 2004/106279 | 12/2004 |
| WO | WO 2005/030678 | 4/2005 |
| WO | WO 2005/049581 | 6/2005 |
| WO | WO 2005/121065 | 12/2005 |
| WO | WO 2005/123692 | 12/2005 |
| WO | WO 2005/123693 | 12/2005 |
| WO | WO 2006/023457 | 3/2006 |
| WO | WO 2006/051375 | 5/2006 |
| WO | WO 2006/122788 | 11/2006 |
| WO | WO 2007/124898 | 11/2007 |
| WO | WO 2008/046598 | 4/2008 |
| WO | WO 2008/095720 | 8/2008 |
| WO | WO 2009/068177 | 6/2009 |
| WO | WO 2009/106351 | 9/2009 |
| WO | WO 2010/072354 | 7/2010 |
| WO | WO 2010/094483 | 8/2010 |
| WO | WO 2010/094484 | 8/2010 |
| WO | WO 2010/102831 | 9/2010 |

OTHER PUBLICATIONS

Patani et al (Chem Rev 96:3147-3176, 1996).*
English Abstract of WO 2002/92606, dated Nov. 21, 2002.
Foye's Principles of Medicinal Chemistry, 4th Edition, pp. 338-340 (1995).
Hashima, H. et al. "Synthesis and Biological Activities of the Marine Byrozoan Alkaloids Convolutamines A, C and F, and Lutamides A and C," Bioorganic & Medicinal Chemistry, 8: 1757-1766 (2000).
U.S. Appl. No. 11/920,561, filed Feb. 11, 2008, Puig Duran et al.
U.S. Appl. No. 12/745,195, filed May 27, 2010, Giulio Matassa et al.
U.S. Appl. No. 12/919,134, filed Oct. 7, 2010, Puig Duran et al.
U.S. Appl. No. 13/141,156, filed Jun. 21, 2011, Carrera Carrera et al.
International Search Report mailed May 7, 2009, for International Application No. PCT/EP2008/009469 (WO 2009/068177).
International Search Report mailed Apr. 21, 2009, for International Application No. PCT/EP2009/001431 (WO 2009/106351).
International Search Report mailed Mar. 2, 2010, for International Application No. PCT/EP2009/008970 (WO 2010/072354).
Interview Summary dated Jun. 11, 2010 for U.S. Appl. No. 11/920,561.
Morissette, SL et al. "High-Throughput Crystallization: Polymorphs, Salts, Co-Crystals and Solvates of Pharmaceutical Solids," Advanced Drug Delivery Reviews, 56: 275-300 (2004).
Notice of Allowance dated Jan. 26, 2011 in U.S. Appl. No. 11/920,561.
Office Action dated Jun. 2, 2010 in U.S. Appl. No. 11/920,561.
Office Action (Quayle Action) dated Nov. 9, 2010 in U.S. Appl. No. 11/920,561.
Office Action dated Mar. 9, 2011 in U.S. Appl. No. 12/745,195.
Office Action dated Apr. 25, 2011 in U.S. Appl. No. 12/298,131.
Office Action dated Jul. 15, 2011 in U.S. Appl. No. 12/745,195.
Office Action dated Jul. 7, 2011 in U.S. Appl. No. 12/444,935.
Patani, GA et al. "Bioisosterism: A Rational Approach in Drug Design," Chem. Rev. 96: 314-3176 (1996).
Restriction Requirement dated Mar. 16, 2010 in U.S. Appl. No. 11/920,561.
Restriction Requirement dated Jan. 5, 2011 in U.S. Appl. No. 12/745,195.
Restriction Requirement dated May 13, 2011 in U.S. Appl. No. 12/444,935.
Silverman, RB "The Organic Chemistry of Drug Design and Drug Action," Academic Press, Chapter 2, pp. 10-23 (1992).
Sterling, J. et al. "Novel Dual Inhibitors of AChE and MAO Derived from Hydroxy Aminoindan and Phenethylamine as Potential Treatment for Alzheimer's Disease," J. Med. Chem. 45(24): 5260-5279 (2002).
Vippagunta, SR et al. "Crystalline Solids," Advanced Drug Delivery Reviews, 48: 3-26 (2001).
U.S. Appl. No. 12/298,131, filed Oct. 22, 2008, Puig duran et al.
U.S. Appl. No. 12/444,935, filed Apr. 9, 2009, Bach Tana et al.
Bastin, RD et al. "Salt Selection and Optimisation for Pharmaceutical New Chemical Entities," Organic Process Research and Development, 4(5): 427-435 (2000).
Caplus English Abstract of DE 2 236 272, Accession No. 1973:405128.
Caplus English Abstract of DE 2 310 140, Accession No. 1975:31115.
Caplus English Abstract of JP 51 149 282, Accession No. 1977:468184.
Caplus English Abstract of JP 59 093 051, Accession No. 1985:45790.
Caplus English Abstract of journal article by Meglio, P. et al. Accession No. 1980:426036.
Coleman, R.A. et al. "Novel and Versatile Superfusion System," *Journal of Pharmacological Methods*, 21: 71-86 (1989).
Cortijo, J. et al. "Effects of dantrolene on the responses to methylxanthines in the isolated guinea-pig trachea," European Journal of Pharmacology 198: 171-176 (1991).

Curran, P.K. et al. "Endogenous $\beta_2$-But Not $\beta_1$-Adrenergic Receptors Are Resistant to Agonist-Mediated Regulation in Human SK-N-MC Neurotumor Cells," *Cell. Signal.*, 8(5): 355-364 (1996).

Deyrup, M.D. et al. "Structure-affinity profile of 8-hydroxycarbostyril-based agonists that dissociate slowly from the $\beta$2-adrenoceptor," Naunyn-Schmiedeberg's Archives of Pharmacology, 359: 168-177(1999).

Furuie, H. et al. "Suppressive effect of novel phosphodiesterase4 (PDE4) inhibitor ONO-6126 on TNF-$\alpha$ release was increased after repeated oral administration in healthy Japanese subjects," *Eur. Resp. Journal*, 22(Supp. 45):Abstract 2557 (2003).

Ismail, FMD. "Important fluorinated drugs in experimental and clinical use," Journal of Fluorine Chemistry 118:27-33 (2002).

Hart, D.J. "A Synthesis of (±)-Gephyrotoxin," *Journal of Organic Chemistry*, 46:3576-3578 (1981).

Hart, D.J. et al. "Total Syntheses of *dl*-Gephyrotoxin and *dl*-Dihydrogephyrotoxin," *J. American Chem. Society*, 105(5): 1255-1263 (1983).

Hett, R. et al. "Enantioselective Synthesis of Salmeterol via Asymmetric Borane Reduction," *Tetrahedron Letters*, 35(50): 9375-9378 (1994).

Hett, R. et al. "Large-Scale Synthesis of Enantio- and Diastereomerically Pure (*R,R*)-Formoterol," *Organic Process Research & Development*, 2(2): 96-99 (1998).

International Search Report mailed Sep. 12, 2006, for International Application No. PCT/EP2006/004680 (WO 2006/122788 A1).

International Search Report mailed Jun. 21, 2007, for International Application No. PCT/EP2007/003601 (WO 2007/124898 A1).

International Search Report mailed Mar. 19, 2008, for International Application No. PCT/EP2007/008992 (WO 2008/046598 A1).

International Search Report mailed May 28, 2008, for International Application No. PCT/EP2008/000975 (WO 2008/095720).

Kaiser, C. et al. "Adrenergic Agents. 1. Synthesis and Potential $\beta$-Adrenergic Agonist Activity of Some Catecholamine Analogs Bearing a Substituted Amino Functionality in the Meta Position," *Journal of Medicinal Chemistry*, 17(1): 49-57 (1974).

Meglio, P. et al. "Synthesis and pharmacological study of orciprenaline and salbutamol derivatives," Farmaco, Edizione Scientifica, 35(3): 203-230 (1980).

Meyers, A.I. et al. "Oxazolines. XI. Synthesis of Functionalized Aromatic and Aliphatic Acids. A Useful Protecting Group for Carboxylic Acids against Grignard and Hydride Reagents," *Journal of Organic Chemistry*, 39(18): 2787-2793 (1974).

Meyers, A.I. et al. "Substitutions on 1-Methoxynaphthalenes via their Oxazoline Derivatives: A Convenient Route to 1-Substituted Naphthoic Acids," *Synthesis Communications*, 2:105-107 (1983).

Murase, K. et al. "New $\beta$-Adrenoreceptor Stimulants. Studies on 3-Acylamino-4-hydroxy-$\alpha$-(N-substituted aminomethyl)benzyl Alcohols," *Chem. Pharm. Bull.*, 25(6): 1368-1377 (1977).

Nielsen, K.G. et al. "Flow-dependent effect of formoterol dry-powder inhaled from the Aerolizer®," *Eur. Respir. Journal*, 10: 2105-2109 (1997).

Portoghese, P.S. "Stereochemical Studies on Medicinal Agents. 19. X-Ray Crystal Structures of Two (±)-Allylprodine Diastereomers. The Role of the Allyl Group in Conferring High Stereoselectivity and Potency at Analgetic Receptors," *Journal of Medicinal Chemistry*, 19(1): 55-57 (1976).

Smart, BE. "Fluorine substituent effects (on bioactivity)," Journal of Fluorine Chemistry 109:3-11 (2001).

Svenson, R. et al. "On the Hydrozirconation of Some Long-Chain Unsaturated Fatty Acid Oxazolines," *Chemica Scripta.*, 19: 149-153 (1982).

Yang, Z. et al. "A Novel and Practical Method for the Preparation of $\alpha,\alpha$-Difluoro Functionalized Esters," *J. Chem. Soc., Chem. Commun.*, 3: 233-234 (1992).

Yang, Z. "Synthesis of new $\alpha,\alpha,\beta,\beta$-tetrafluoroesters," *Journal of Fluorine Chemistry*, 125: 763-765 (2004).

Yoshizaki, S. et al. "Sympathomimetic Amines having a 3,4-Dihydrocarbostyril Nucleus," Chemical and Pharmaceutical Bulletin, 26(5): 1611-1614 (1978).

Yoshizaki, S. et al. "Sympathomimetic Amines Having a Carbostyril Nucleus," *Journal of Medicinal Chemistry*, 19(9): 1138-1142 (1976).

Dexamethasone, Merck Index, Monograph No. 02943 (2011).

Han, J. "Advances in Characterization of Pharmaceutical Hydrates," Trends in Bio/Pharmaceutical Industry, 3:25-29 (2006).

International Search Report mailed May 25, 2010, for International Application No. PCT/EP2010/001027 (WO 2010/094484).

International Search Report mailed May 27, 2010, for International Application No. PCT/EP2010/001026 (WO 2010/094483).

U.S. Appl. No. 13/202,020, filed Oct. 18, 2011, Ruf et al.

U.S. Appl. No. 13/202,025, filed Oct. 14, 2011, Ruf et al.

U.S. Appl. No. 13/255,621, filed Sep. 19, 2011, Hereu et al.

International Search Report mailed Sep. 16, 2010, for International Application No. PCT/EP2010/001582 (WO 2010/102832).

Interview Summary dated Feb. 22, 2012, for U.S. Appl. No. 12/745,195.

Johnson, M. "Salmeterol," Medicinal Research Reviews, 15(3): 225-257 (1995).

Kikkawa, H. et al. "Differential contribution of two serine residues of wild type and constitutively active $\beta_2$-adrenoreceptors to the interaction with $\beta_2$-selective agonists," British Journal of Pharmacology, 121: 1059-1064 (1997).

Notice of Allowance dated Dec. 28, 2011 in U.S. Appl. No. 12/745,195.

Notice of Allowance dated Feb. 24, 2012 in U.S. Appl. No. 12/745,195.

Office Action (Restriction Requirement) dated Dec. 29, 2011 in U.S. Appl. No. 13/094,156.

Office Action dated Jan. 26, 2012 in U.S. Appl. No. 12/298,131.

Office Action dated Jan. 30, 2012 in U.S. Appl. No. 12/444,935.

Office Action (Quayle Action) dated Feb. 14, 2012, in U.S. Appl. No. 13/094,156.

STN Search Report, Accession No. 2003:875242, CAS RN 620599-83-9 (2011).

\* cited by examiner

Figure 1: X-Ray Powder Diffraction (XRPD) pattern of 5-(-2-(6-(2,2-Difluoro-2-phenylethoxy)hexylamino)-1(R)-hydroxyethyl)-8-hydroxyquinolin-2(1H)-one heminapadisylate.
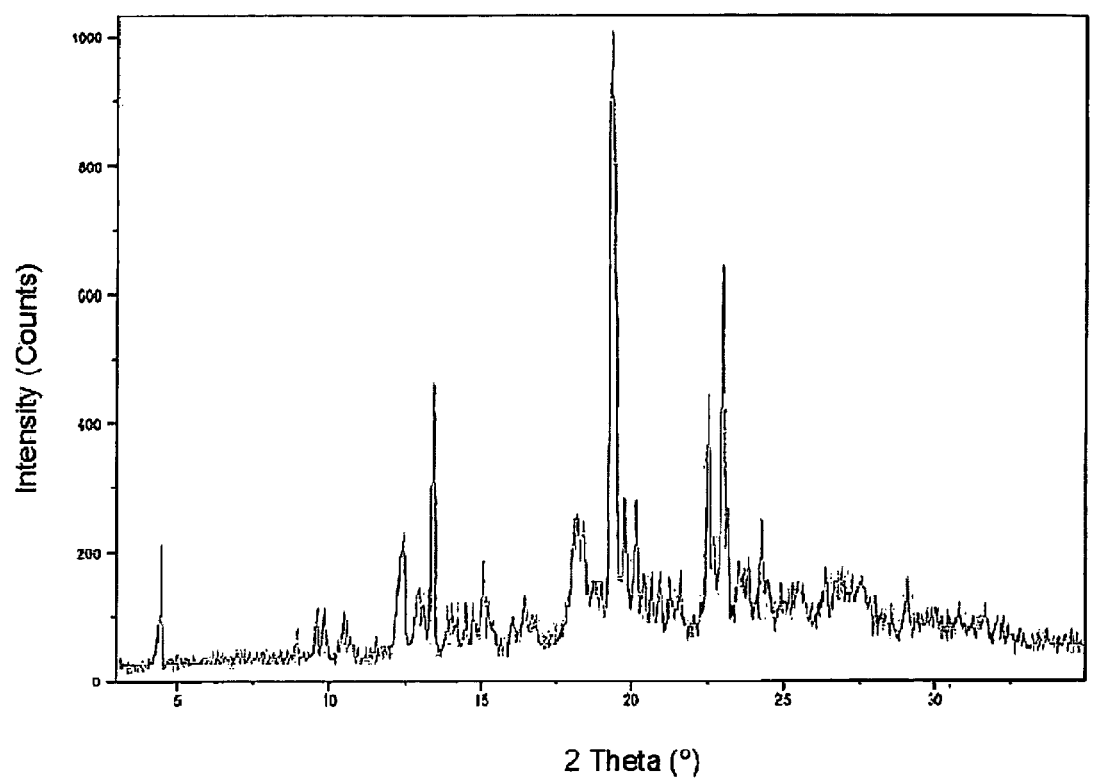

Figure 2: DSC pattern of 5-(-2-(6-(2,2-Difluoro-2-phenylethoxy) hexylamino)-1(R)-hydroxyethyl)-8-hydroxyquinolin-2(1H)-one heminapadisylate.
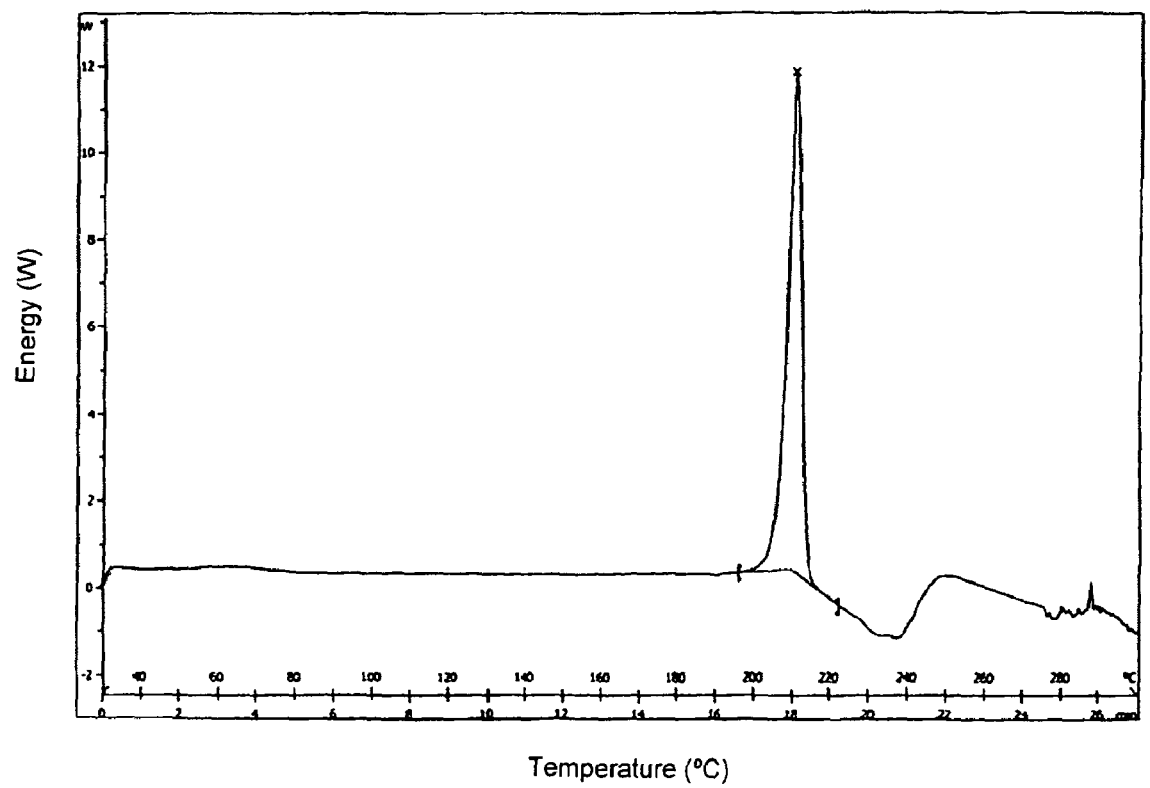

Figure 3: TGA pattern of 5-(-2-(6-(2,2-Difluoro-2-phenylethoxy)hexylamino)-1(R)-hydroxyethyl)-8-hydroxyquinolin-2(1H)-one heminapadisylate.
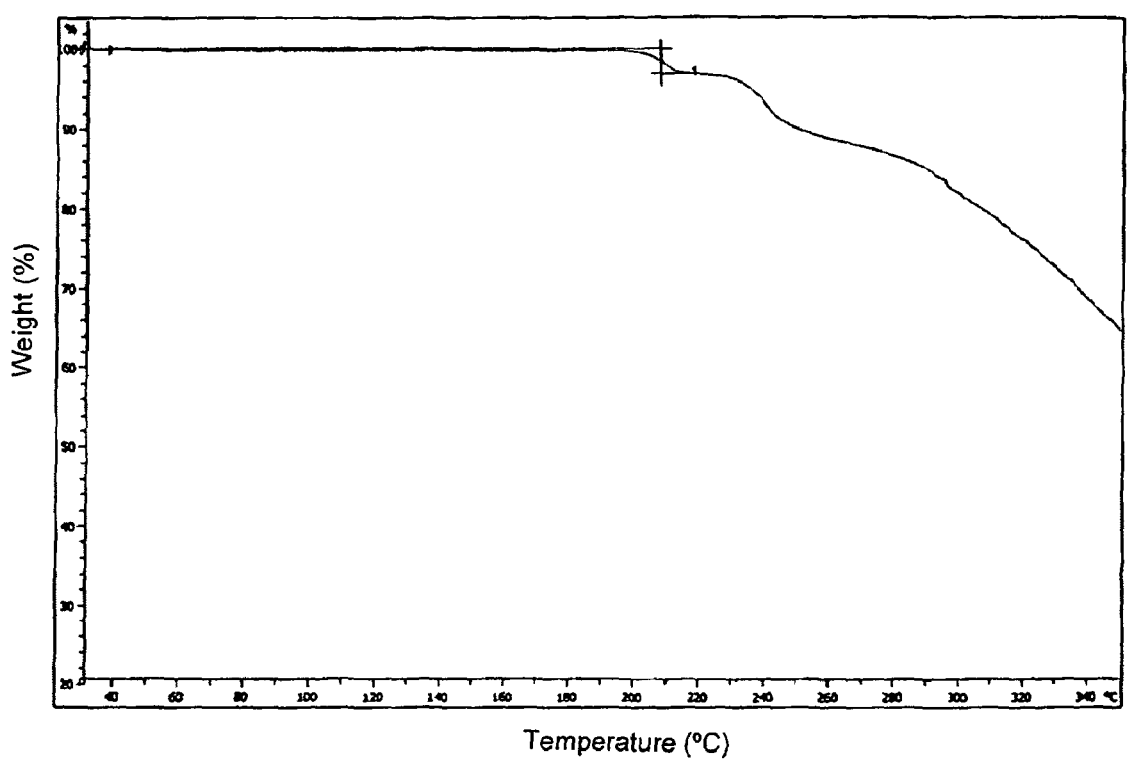

NAPADISYLATE SALT OF 5-(2-{[6-(2,2-DIFLUORO-2-PHENYLETHOXY) HEXYL] AMINO}-1-HYDROXYETHYL)-8-HYDROXYQUINOLIN-2(1H)-ONE AS AGONIST OF THE β2 ADRENERGIC RECEPTOR

This application is a national stage filing under 35 U.S.C. §371 of International Application No. PCT/EP2008/000975 filed on 8 Feb. 2008, which claims priority of Spanish Patent Application No. P200700362, filed on 9 Feb. 2007. The contents of both applications are incorporated herein by reference.

FIELD OF THE INVENTION

The present invention is directed to novel crystalline naphthalene-1,5-disulfonic acid salts (napadisylates) of 5-(2-{[6-(2,2-difluoro-2-phenylethoxy)hexyl]amino}-1-hydroxyethyl)-8-hydroxyquinolin-2(1H)-one, its enantiomers and solvates thereof. The invention is also directed to pharmaceutical compositions comprising the crystalline salts, methods of using them to treat respiratory diseases associated with β2 adrenergic receptor activity, and processes and intermediates useful for preparing such salts.

BACKGROUND OF THE INVENTION

β2 adrenergic receptor agonists are advantageously administered directly into the respiratory tract by inhalation when used for treating pulmonary or respiratory disorders. Several types of pharmaceutical inhalation devices have been developed for administering therapeutic agents by inhalation including dry powder inhalers (DPI), metered-dose inhalers (MDI) and nebulizer inhalers. It is highly desirable to have a crystalline form of the β2 adrenergic receptor agonists that is neither hygroscopic nor deliquescent and which has a relatively high melting point thereby allowing the material to be micronized without significant decomposition or loss of crystallinity to prepare the pharmaceutical compositions and formulations for use in such devices.

5-(2-{[6-(2,2-difluoro-2-phenylethoxy)hexyl]amino}-1-hydroxyethyl)-8-hydroxyquinolin-2(1H)-one is claimed and described in published patent application WO 2006/122788 A1.

Although the 5-(2-{[6-(2,2-difluoro-2-phenylethoxy)hexyl]amino}-1-hydroxyethyl)-8-hydroxyquinolin-2(1H)-one has shown adequate pharmacological behaviour it has proved difficult to obtain it in the form of a salt which is crystalline, not hygroscopic nor deliquescent and which has a relatively high melting point to enable micronization.

So far no crystalline salt of 5-(2-{[6-(2,2-difluoro-2-phenylethoxy)hexyl]amino}-1-hydroxyethyl)-8-hydroxyquinolin-2(1H)-one having the desired properties has been reported.

Accordingly, a need exists for stable, non-deliquescent salt forms of this compound which has acceptable levels of hygroscopicity and relatively high melting points.

SUMMARY OF THE INVENTION

It has now been found that naphthalene-1,5-disulfonic acid salts of 5-(2-{[6-(2,2-difluoro-2-phenylethoxy)hexyl]amino}-1-hydroxyethyl)-8-hydroxyquinolin-2(1H)-one can be obtained in a crystalline form which is neither hygroscopic nor deliquescent and which has a relatively high melting point thereby allowing the material to be micronized without significant decomposition or loss of crystallinity.

The present invention provides a crystalline mononapadisylate and/or heminapadisylate salt of 5-(2-{[6-(2,2-difluoro-2-phenylethoxy)hexyl]amino}-1-hydroxyethyl)-8-hydroxyquinolin-2(1H)-one and pharmaceutically acceptable solvates thereof.

Typically, the crystalline naphthalene-1,5-disulfonic acid salts of the invention have the formula (I):

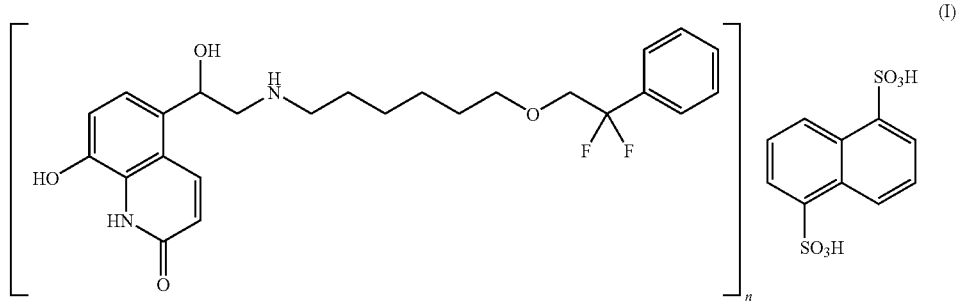

(I)

wherein n has a value of 1 or 2.

The present invention particularly provides the crystalline salt as a mononapadisylate salt or as a heminapadisylate salt and solvates thereof.

The invention also provides a pharmaceutical composition comprising a salt of the invention and a pharmaceutically-acceptable carrier. The invention further provides combinations comprising a salt of the invention and one or more other therapeutic agents and pharmaceutical compositions comprising such combinations.

The invention also provides a method of treating a pulmonary disease or condition associated with β2 adrenergic receptor activity such as asthma or chronic obstructive pulmonary disease, in a mammal, comprising administering to the mammal, a therapeutically effective amount of a salt of the invention. The invention further provides a method of treatment comprising administering a therapeutically effective amount of a combination of a salt of the invention together with one or more other therapeutic agents.

The invention further provides synthetic processes and intermediates described herein, which are useful for preparing salts of the invention.

The invention also provides a salt of the invention as described herein for use in medical therapy, as well as the use of a salt of the invention in the manufacture of a formulation or medicament for treating a pulmonary disease or condition associated with β2 adrenergic receptor activity such as asthma or chronic obstructive pulmonary disease in a mammal.

BRIEF DESCRIPTION OF FIGURES

FIG. 1 shows the X-Ray Powder Diffraction (XRPD) pattern of 5-(2-(6-(2,2-Difluoro-2-phenylethoxy)hexylamino)-1(R)-hydroxyethyl)-8-hydroxyquinolin-2(1H)-one heminapadisylate. The figures on the Y axis are intensity (counts). The figures on the X axis show 2 Theta (°).

FIG. 2 shows the DSC pattern of 5-(2-(6-(2,2-Difluoro-2-phenylethoxy)hexylamino)-1(R)-hydroxyethyl)-8-hydroxyquinolin-2(1H)-one heminapadisylate. The figures on the Y axis are energy (W). The figures on the X axis are temperature (° C.).

FIG. 3 shows the TGA pattern of 5-(2-(6-(2,2-Difluoro-2-phenylethoxy)hexylamino)-1(R)-hydroxyethyl)-8-hydroxyquinolin-2(1H)-one heminapadisylate. The figures on the Y axis are weight (%). The figures on the X axis are temperature (° C.).

DETAILED DESCRIPTION OF THE INVENTION

When describing the salts, compositions and methods of the invention, the following terms have the following meanings, unless otherwise indicated.

The term "therapeutically effective amount" refers to an amount sufficient to effect treatment when administered to a patient in need of treatment.

The term "treatment" as used herein refers to the treatment of a disease or medical condition in a human patient which includes:

(a) preventing the disease or medical condition from occurring, i.e., prophylactic treatment of a patient;

(b) ameliorating the disease or medical condition, i.e., causing regression of the disease or medical condition in a patient;

(c) suppressing the disease or medical condition, i.e., slowing the development of the disease or medical condition in a patient; or (d) alleviating the symptoms of the disease or medical condition in a patient.

The phrase "pulmonary disease or condition associated with β2 adrenergic receptor activity" includes all pulmonary disease states and/or conditions that are acknowledged now, or that are found in the future, to be associated with β2 adrenergic receptor activity.

Such disease states include, but are not limited to asthma and chronic obstructive pulmonary disease (including chronic bronchitis and emphysema).

The term "solvate" refers to a complex or aggregate formed by one or more molecules of a solute, i.e. a salt of the invention or a pharmaceutically-acceptable salt thereof, and one or more molecules of a solvent. Such solvates are typically crystalline solids having a substantially fixed molar ratio of solute and solvent. Representative solvents include by way of example, water, ethanol, isopropanol and the like. When the solvent is water, the solvate formed is a hydrate.

It will be appreciated that the term "or solvate or stereoisomer thereof" is intended to include all permutations of solvates and stereoisomers, such as a solvate of a stereoisomer of a salt of formula (I).

The salts of the invention contain a chiral center. Accordingly, the invention includes racemic mixtures, enantiomers, and mixtures enriched in one of the enantiomers. The scope of the invention as described and claimed encompasses the racemic forms of the salts as well as the individual enantiomers and enantiomer-enriched mixtures.

Of particular interest are the salts:

(R,S)5-(2-{[6-(2,2-difluoro-2-phenylethoxy)hexyl]amino}-1-hydroxyethyl)-8-hydroxyquinolin-2(1H)-one, napadisylate 5-(2-{[6-(2,2-difluoro-2-phenylethoxy)hexyl]amino}-1(R)-hydroxyethyl)-8-hydroxyquinolin-2(1H)-one, napadisylate (R,S)5-(2-{[6-(2,2-difluoro-2-phenylethoxy)hexyl]amino}-1-hydroxy-ethyl)-8-hydroxyquinolin-2(1H)-one, heminapadisylate 5-(2-{[6-(2,2-difluoro-2-phenylethoxy)hexyl]amino}-1(R)-hydroxy-ethyl)-8-hydroxyquinolin-2(1H)-one, heminapadisylate and pharmaceutically acceptable solvates thereof.

Of outstanding interest are the salts:

(R,S)5-(2-{[6-(2,2-difluoro-2-phenylethoxy)hexyl]amino}-1-hydroxy-ethyl)-8-hydroxyquinolin-2(1H)-one, heminapadisylate 5-(2-{[6-(2,2-difluoro-2-phenylethoxy)hexyl]amino}-1(R)-hydroxy-ethyl)-8-hydroxyquinolin-2(1H)-one, heminapadisylate and pharmaceutically acceptable solvates thereof.

In an embodiment of the present invention in the salt of formula (I) n has the value of 2.

The invention also encompasses pharmaceutical compositions comprising a therapeutically effective amount of a salt as hereinabove defined and a pharmaceutically acceptable carrier.

In an embodiment of the present invention the pharmaceutical composition further comprises a therapeutically effective amount of one or more other therapeutic agents.

It is also an embodiment of the present invention that the pharmaceutical composition is formulated for administration by inhalation.

The salts of the present invention as hereinabove defined may also be combined with one or more other therapeutic agents, in particular one or more drugs selected from the group consisting of corticosteroids, anticholinergic agents and PDE4 inhibitors.

The invention is also directed to a method of treating a disease or condition in a mammal associated with β2 adrenergic receptor activity, the method comprising administering to the mammal, a therapeutically effective amount of a pharmaceutical composition comprising a β2 adrenergic receptor agonist according to the present invention. It is of particular relevance the method applied to the treatment of a disease or condition which is a pulmonary disease, preferably asthma or chronic obstructive pulmonary disease.

The invention is also directed to the use of a salt of formula (I) in the manufacture of a medicament for the treatment of a pulmonary disease or condition in a mammal. The mammal is preferably a human being. Particularly relevant pulmonary diseases or conditions are asthma or chronic obstructive pulmonary disease.

The invention is also directed to a salt of formula (I) for use in the treatment of a pulmonary disease or condition. The mammal is preferably a human being. Particularly relevant pulmonary diseases or conditions are asthma or chronic obstructive pulmonary disease.

General Synthetic Procedures

The salts of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Processes for preparing salts of the invention are provided as further embodiments of the invention and are illustrated by the procedures below.

The crystalline salts of the invention can be synthesized from 5-(2-{[6-(2,2-difluoro-2-phenylethoxy)hexyl]amino}-1-hydroxyethyl)-8-hydroxyquinolin-2(1H)-one and from naphthalene-1,5-disulfonic acid (also known as Armstrong's Acid) or from its tetrahydrate which are commercially available from, for example, Aldrich.

Suitable inert diluents for this reaction include, but are not limited to, acetone, dimethylformamide, methanol, ethanol, isopropanol, isobutanol, ethyl acetate, acetic acid and the like, and mixtures thereof, optionally containing water. For example, the free base can be contacted with anhydrous naphthalene-1,5-disulfonic acid, dissolved in methanol.

Upon completion of any of the foregoing reactions, the crystalline salts can be isolated from the reaction mixture by any conventional means such as precipitation, concentration, centrifugation and the like.

It will be appreciated that while specific process conditions (i.e. reaction temperatures, times, mole ratios of reactants, solvents, pressures, etc.) are given, other process conditions can also be used unless otherwise stated.

A crystalline mononapadisylate salt of the invention typically contains between about 0.8 and 1.2 molar equivalents of naphthalene-1,5-disulfonic acid per molar equivalent of the free base, more typically about 1.0 molar equivalents of naphthalene-1,5-disulfonic acid per molar equivalent of the free base.

A crystalline heminapadisylate salt of the invention typically contains between about 0.35 and 0.65 molar equivalents of naphthalene-1,5-disulfonic acid per molar equivalent of the free base, more typically about 0.5 molar equivalents of naphthalene-1,5-disulfonic acid per molar equivalent of the free base.

The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

To prepare a crystalline heminapadisylate salt, the free base is typically dissolved in a solvent such as acetonitrile, dimethylformamide, methanol, ethanol, isopropanol, isobutanol, ethyl acetate, acetic acid and mixtures thereof, particularly in methanol to form a 0.10-0.12M solution which is heated to approximately 45-55° C. 0.05-0.06 mols of naphthalene-1,5-disulfonic acid tetrahydrate per liter of base solution are added to the heated solution. The mixture is then stirred for 30 minutes at reflux temperature and then cooled down to 20/25° C. and stirred at this temperature for 1 additional hour. The precipitate formed is isolated by filtration, washed with an appropriate solvent such as methanol and dried for example in vacuum at 50° C.

EXAMPLES

General. Reagents, starting materials, and solvents were purchased from commercial suppliers and used as received.

Crystallizations test of salts of 5-(2-{[6-(2,2-difluoro-2-phenylethoxy)hexyl]amino}-1(R)-hydroxyethyl)-8-hydroxyquinolin-2(1H)-one with a broad range of pharmaceutically acceptable acids (comprising among others fumaric, succinic, sulphuric, 1-hydroxy-2-naphthoic, L-tartaric, D-tartaric, hydrochloric, methylsulfonic, p-toluensulfonic, naphthalensulfonic, L-mandelic, D,L-mandelic, citric, 1S-camphor-10-sulfonic, L-malic, L-aspartic, L-piroglutamic and 1,5-disulfonic acids) in a range of different pharmaceutically acceptable solvents (including among others acetone, acetonitrile, ethyl acetate, isobutyl acetate, 2-butanol, chloroform, dichloromethane, dioxane, dimethylformamide, ethanol, water, isopropanol, methyl ethyl ketone, methanol, tetrahydrofurane and toluene) have been undertaken.

Only a few of these tests have yielded crystalline salts. From these crystalline salts only the napadisylate salts were neither hygroscopic nor deliquescent and had a relatively high melting point allowing them to be micronized and to have a long term stability.

A particularly good method to prepare a 5-(2-{[6-(2,2-difluoro-2-phenylethoxy)hexyl]amino}-1(R)-hydroxyethyl)-8-hydroxyquinolin-2(1H)-one heminapadisylate salt comprises dissolving 14.4 mmols of free base in 134 ml of methanol to form a 1.075 M solution which is heated to approximately 50° C. Then, 7.74 mmols of naphthalene-1,5-disulfonic acid tetrahydrate are added to the heated solution. The mixture is then stirred for 30 minutes at reflux temperature and then cooled down to 20/25° C. and stirred at this temperature for 1 additional hour. The precipitate formed is isolated by filtration, washed with methanol and dried in vacuum at 50° C.

X-Ray Powder Diffraction (XRPD) analysis was performed on a Panalytical X-ray powder diffractometer, model X'Pert PRO MPD. The method runs from 2 to 50 degrees 2-Theta with a 0.017 degree 2-Theta step size and a 300 second collection time at each step using an X'celerator detector.

FIG. 1 shows an XRPD pattern of the salt 5-(-2-(6-(2,2-Difluoro-2-phenylethoxy)hexylamino)-1(R)-hydroxyethyl)-8-hydroxyquinolin-2(1H)-one heminapadisylate, which confirms the crystallinity of the sample.

The differential scanning calorimetry (DSC) analysis was obtained using a DSC-821 Mettler-Toledo, serial number 5117423874. Samples were weighed into an aluminium pan, an aluminium lid placed on top of the sample and compressed with a brass rod. Samples were equilibrated at 30° C. and heated at 10° C./min to 300° C. The instrument was calibrated using indium and zinc standards.

FIG. 2 shows a DSC pattern of the salt 5-(-2-(6-(2,2-Difluoro-2-phenylethoxy)hexylamino)-1(R)-hydroxyethyl)-8-hydroxyquinolin-2(1H)-one heminapadisylate. The sample exhibits an endotherm with an onset of around 206° C. and there are no changes prior to the melting point range. This indicates that the sample does not convert into any other polymorphs and does not suffer any decomposition, confirming thus its high stability The thermogravimetric (TGA) analysis was obtained using a TGA-SDTA-851 Mettler-Toledo, serial number 5118408555. Samples were placed into a tared aluminium pan and then positioned on a platinum crucible. Samples were heated from 30° C. at 10° C./min to 350° C. The instrument was calibrated using indium and aluminium standards.

FIG. 3 shows a TGA pattern of 5-(-2-(6-(2,2-Difluoro-2-phenylethoxy)hexylamino)-1(R)-hydroxyethyl)-8-hydroxyquinolin-2(1H)-one heminapadisylate. The sample exhibits a weight loss of 3.1% w/w from approximately 200° C. to 220° C. due to the decomposition of the sample. Prior to 200° C., and in particular at the temperature range of 80-100° C., the sample does not exhibit any change. This indicates that there is no solvent/water release, confirming thus the lack of hygroscopicity of the sample.

Pharmaceutical Compositions

Pharmaceutical compositions according to the present invention comprise a therapeutically effective amount of a napadisylate salt of 5-(2-{[6-(2,2-difluoro-2-phenylethoxy)hexyl]amino}-1-hydroxyethyl)-8-hydroxyquinolin-2(1H)-one or an enantiomer or pharmaceutically acceptable solvate thereof and a pharmaceutically acceptable carrier.

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the salt of the invention and a suitable powder base (carrier substance) such as lactose or starch. Use of lactose is preferred.

Each capsule or cartridge may generally contain between 2 µg and 150 µg of each therapeutically active ingredient. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

Effective doses are normally in the range of 1-2000 µg of active ingredient per day. Daily dosage may be administered in one or more treatments, preferably from 1 to 4 treatments, per day.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatin capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, *Eur. Resp. Journal*, 10: 2105-2109 ((1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e. g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (e. g. EP0069715) or disks (e. g. GB 2041763; EP 0424790; DE 4239402 and EP 0674533), rotatable cylinders (e. g. EP 0166294; GB 2165159 and WO 92/09322) and rotatable frustums (e. g. WO 92/00771), all having cavities which have to be filled with powder from the container. Other multi dose devices have measuring plungers with a local or circumferential recess to displace a certain volume of powder from the container to a delivery chamber or an air conduit (e. g. EP 0505321, WO 92/04068 and WO 92/04928), or measuring slides such as the Novolizer SD2FL (ex. Sofotec) which is described in the following patent applications: WO 97/000703, WO 03/000325 and WO 03/061742.

Reproducible dose measuring is one of the major concerns for multi dose inhaler devices. The powder formulation has to exhibit good and stable flow properties, because filling of the dose measuring cups or cavities is mostly under the influence of the force of gravity. For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e. g. WO 97/000703). For such semi-permanent multi dose inhalers with disposable drug containers, the requirements to prevent drug accumulation are even more strict.

Medicaments for administration by inhalation desirably have a controlled particle size. The optimum particle size for inhalation into the bronchial system is usually 1-10µ, preferably 2-5µ. Particles having a size above 20µ are generally too large when inhaled to reach the small airways. To achieve these particle sizes, the particles of the active ingredient as produced may be size reduced by conventional means eg by micronisation. The desired fraction may be separated out by air classification or sieving. Preferably, the particles will be crystalline.

Apart from applications through dry powder inhalers the compositions of the invention can also be administered in aerosols which operate via propellant gases or by means of so-called atomisers, via which solutions of pharmacologically-active substances can be sprayed under high pressure so that a mist of inhalable particles results. Such atomisers are described, for example, in WO 91/14468 and WO 97/12687.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate. Pressurized aerosol compositions will generally be filled into canisters fitted with a valve, especially a metering valve. Canisters may optionally be coated with a plastics material e. g. a fluorocarbon polymer as described in WO96/32150. Canisters will be fitted into an actuator adapted for buccal delivery.

Each dosage unit contains suitably from 1 µg to 100 µg, and preferably from 5 µg to 50 µg of a β2-agonist according to the invention.

The compositions of the invention can optionally comprise a therapeutically effective amount of one or more other therapeutic agents which are known to be useful in the treatment of respiratory disorders, such as PDE4 inhibitors, corticosteroids and/or anticholinergics.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day, most preferably once a day.

Examples of suitable PDE4 inhibitors that can be combined with β2-agonists are denbufylline, rolipram, cipamfylline, arofylline, filaminast, piclamilast, mesopram, drotaverine hydrochloride, lirimilast, roflumilast, cilomilast, oglemilast, apremilast, 6-[2-(3,4-diethoxyphenyl)thiazol-4-yl]pyridine-2-carboxylic acid (tetomilast), (R)-(+)-4-[2-(3-Cyclopentyloxy-4-methoxyphenyl)-2-phenylethyl]pyridine, N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine, N-(3,5-Dichloro-4-pyridinyl)-8-methoxyquinoline-5-carboxamide, N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride, 4-[6,7-Diethoxy-2,3-bis(hydroxymethyl)naphthalen-1-yl]-1-(2-methoxyethyl)pyridin-2(1H)-one, 2-carbomethoxy-4-cyano-4-(3-cyclopropylmethoxy-4-difluoromethoxyphenyl)cyclohexan1-one, cis[4-cyano-4-(3-cyclopropylmethoxy-4-difluoromethoxyphenyl)cyclohexan-1-ol, ONO-6126 (Eur Respir J 2003, 22(Suppl. 45): Abst 2557) and the salts claimed in the PCT patent application numbers WO03/097613, WO2004/058729, WO 2005/049581, WO 2005/123693 and WO 2005/123692.

Examples of suitable corticosteroids and glucocorticoids that can be combined with β2-agonists are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, butixocort propionate, RPR-106541, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Examples of suitable M3 antagonists (anticholinergics) that can be combined with β2-agonists are tiotropium salts, oxitropium salts, flutropium salts, ipratropium salts, glycopyrronium salts, trospium salts, revatropate, espatropate, 3-[2-Hydroxy-2,2-bis(2-thienyl)acetoxy]-1-(3-phenoxypropyl)-1-azoniabicyclo[2.2.2]octane salts (in particular aclidinium salts, more preferably aclidinium bromide), 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N-[N-[2-[N-[1-(Cyclohexylmethyl)piperidin-3(R)-ylmethyl]carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Particularly preferred pharmaceutical composition according to the invention comprise a salt of formula (I) and a therapeutically effective amount of one or more additional therapeutic agents selected from the group consisting of mometasone furoate, ciclesonide, budesonide, fluticasone propionate, fluticasone furoate, tiotropium salts, glycopyrronium salts, 3-[2-Hydroxy-2,2-bis(2-thienyl)acetoxy]-1-(3-phenoxypropyl)-1-azoniabicyclo[2.2.2]octane salts (in particular aclidinium salts, preferably aclidinium bromide), 1-(2-Phenylethyl)-3-(9H-xanthen-9-ylcarbonyloxy)-1-azoniabicyclo[2.2.2]octane salts, rolipram, roflumilast, cilomilast and the compounds claimed in the PCT patent application numbers WO03/097613, WO2004/058729, WO 2005/049581, WO 2005/123693 and WO 2005/123692

Thus, in one aspect of the invention, the composition comprises a salt of formula (I) and a corticosteroid. Particularly preferred corticosteroids are those selected from the group consisting of mometasone furoate, ciclesonide, budesonide, fluticasone furoate and fluticasone propionate.

In another aspect of the invention, the composition comprises a salt of formula (I) and an anticholinergic agent. Particulary preferred anticholinergic agents are those selected from the group consisting of tiotropium salts, glycopirronium salts, 3-[2-Hydroxy-2,2-bis(2-thienyl)acetoxy]-1-(3-phenoxypropyl)-1-azoniabicyclo[2.2.2]octane salts and 1-(2-Phenylethyl)-3-(9H-xanthen-9-ylcarbonyloxy)-1-azoniabicyclo[2.2.2]octane salts. The composition may further comprise a corticosteroid selected from the group consisting of mometasone furoate, ciclesonide, budesonide, fluticasone furoate and fluticasone propionate.

In a still other aspect of the invention, the composition comprises a salt of formula (I) and a PDE4 inhibidor. Particularly preferred PDE4 inhibidors are those selected from the group consisting of rolipram, roflumilast, cilomilast and the compounds claimed in the PCT patent application numbers WO03/097613, WO2004/058729, WO 2005/049581, WO 2005/123693 and WO 2005/123692. The composition may further comprise a corticosteroid selected from the group consisting of mometasone furoate, ciclesonide, budesonide, fluticasone furoate and fluticasone propionate. In addition to the salt of the invention and to the PDE4 inhibitor, the composition may further comprise an anticholinergic agent selected from the group consisting of tiotropium salts, glycopirronium salts, 3-[2-Hydroxy-2,2-bis(2-thienyl)acetoxy]-1-(3-phenoxypropyl)-1-azoniabicyclo[2.2.2]octane salts and 1-(2-Phenylethyl)-3-(9H-xanthen-9-ylcarbonyloxy)-1-azoniabicyclo[2.2.2]octane salts.

In a particularly preferred embodiment of the present invention, the composition comprises a salt of formula (I) and a therapeutically effective amount of a 3-[2-Hydroxy-2,2-bis(2-thienyl)acetoxy]-1-(3-phenoxypropyl)-1-azoniabicyclo[2.2.2]octane salts. Optionally, the composition further comprises a corticosteroid and/or a PDE4 inhibidor.

In another particularly preferred embodiment of the present invention, the composition comprises a salt of formula (I) and a therapeutically effective amount of mometasone furoate. Optionally, the composition further comprises an anticholinergic and/or a PDE4 inhibidor.

In yet another embodiment of the invention, the composition comprises salt of formula (I), a corticosteroid, an anticholinergic agent and a PDE4 inhibidor.

The salts of formula (I) and the combinations of the invention may be used in the treatment of respiratory diseases, wherein the use of bronchodilating agents is expected to have a beneficial effect, for example asthma, acute or chronic bronchitis, emphysema, or Chronic Obstructive Pulmonary Disease (COPD).

The active compounds and the salts in the combination, i.e. the β2-agonist of the invention and the PDE4 inhibitors, corticosteroids or glucocorticoids and/or anticholinergics may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers; however, any other form of topical, parenteral or oral application is possible. Here, the application of inhaled compositions embodies the preferred application form, especially in the therapy of obstructive lung diseases or for the treatment of asthma.

Additional suitable carriers for formulations of the active salts of the present invention can be found in Remington: The Science and Practice of Pharmacy, 20th Edition, Lippincott Williams & Wilkins, Philadelphia, Pa., 2000. The following non-limiting examples illustrate representative pharmaceutical compositions of the invention.

The invention further encompasses a method of treating a pulmonary disease or condition, such as asthma or chronic obstructive pulmonary disease in a mammal associated with β2 adrenergic receptor activity, the method comprising administering to the mammal, a therapeutically effective amount of a pharmaceutical composition as described above.

In particular the method of treating a pulmonary disease or condition comprises administering to the mammal, a therapeutically effective amount of a napadisylate salt of a compound of formula (I) and a therapeutically effective amount of one or more other therapeutic agents, such as a corticosteroid, an anticholinergic agent, or a PDE4 inhibitor.

Formulation Example 1

Gelatin Cartridge for Inhalation

| Ingredient | Amount |
| --- | --- |
| 5-(2-{[6-(2,2-difluoro-2-phenylethoxy)hexyl]amino}-1(R)-hydroxyethyl)-8-hydroxyquinolin-2(1H)-one, napadisylate (micronized) | 0.2 mg |
| Lactose | 25 mg |

Formulation Example 2

Formulation for Inhalation with a DPI

| Ingredient | Amount |
| --- | --- |
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 15 mg |
| Lactose | 3000 mg |

Formulation Example 3

Formulation for Inhalation with a DPI

| Ingredient | Amount |
|---|---|
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 15 mg |
| 3(R)-[2-Hydroxy-2,2-bis(2-thienyl)acetoxy]-1-(3-phenoxypropyl)-1-azoniabicyclo[2.2.2]octane bromide | 100 mg |
| Lactose | 3000 mg |

Formulation Example 4

Formulation for Inhalation with a DPI

| Ingredient | Amount |
|---|---|
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 15 mg |
| Mometasone furoate | 400 mg |
| Lactose | 3000 mg |

Formulation Example 5

Formulation for Inhalation with a DPI

| Ingredient | Amount |
|---|---|
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 15 mg |
| 3(R)-[2-Hydroxy-2,2-bis(2-thienyl)acetoxy]-1-(3-phenoxypropyl)-1-azoniabicyclo[2.2.2]octane bromide | 100 mg |
| Mometasone furoate | 400 mg |
| Lactose | 3000 mg |

Formulation Example 6

Formulation for a MDI

| Ingredient | Amount |
|---|---|
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 10 g |
| 1,1,1,2,3,3,3-heptafluoro-n-propane | q.s. to 200 ml |

The invention claimed is:

1. A salt of 5-(2-{[6-(2,2-difluoro-2-phenylethoxy)hexyl]amino}-1-hydroxyethyl)-8-hydroxyquinolin-2(1H)-one; wherein the salt is a crystalline heminapadisylate salt having the formula:

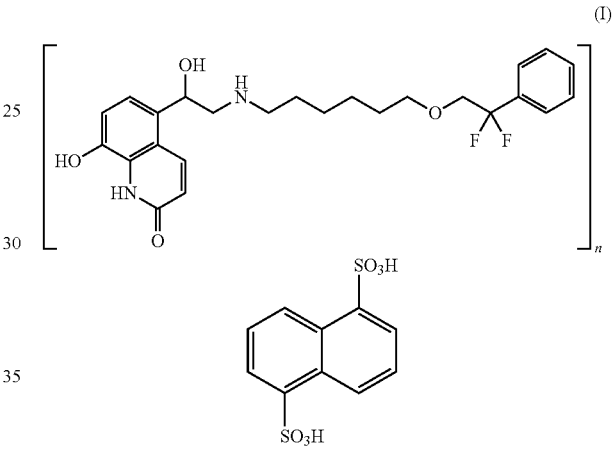

wherein n is 2.

2. The salt according to claim 1, chosen from:
   (R, S) 5-(2-{[6-(2,2-difluoro-2-phenylethoxy)hexyl]amino}-1-hydroxy-ethyl)-8-hydroxyquinolin-2(1H)-one, heminapadisylate; and
   5-(2-{[6-(2,2-difluoro-2-phenylethoxy)hexyl]amino}-1(R)-hydroxy-ethyl)-8-hydroxyquinolin-2(1H)-one, heminapadisylate.

3. A pharmaceutical composition comprising a therapeutically effective amount of a salt according to claim 1 and a pharmaceutically acceptable carrier.

4. The pharmaceutical composition according to claim 3, wherein the composition is formulated for administration by inhalation.

* * * * *